(12) United States Patent
Govyadinov et al.

(10) Patent No.: US 11,364,498 B2
(45) Date of Patent: *Jun. 21, 2022

(54) MICROFLUIDIC DEVICES

(71) Applicant: Hewlett-Packard Development Company, L.P., Spring, TX (US)

(72) Inventors: Alexander Govyadinov, Corvallis, OR (US); Adam Higgins, Corvallis, OR (US); Pavel Kornilovich, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 217 days.

This patent is subject to a terminal disclaimer.

(21) Appl. No.: 16/493,402

(22) PCT Filed: Apr. 7, 2017

(86) PCT No.: PCT/US2017/026571
§ 371 (c)(1),
(2) Date: Sep. 12, 2019

(87) PCT Pub. No.: WO2018/186884
PCT Pub. Date: Oct. 11, 2018

(65) Prior Publication Data
US 2020/0009558 A1    Jan. 9, 2020

(51) Int. Cl.
*B01L 3/00* (2006.01)
*B01L 7/00* (2006.01)

(52) U.S. Cl.
CPC ... *B01L 3/502723* (2013.01); *B01L 3/502746* (2013.01); *B01L 7/525* (2013.01);
(Continued)

(58) Field of Classification Search
CPC .. H04N 17/00; H04N 7/102; B01L 2200/147; B01L 2300/088; B01L 2300/0883;
(Continued)

(56) References Cited

U.S. PATENT DOCUMENTS 6,739,708 B2    5/2004  Studer et al.
7,999,937 B1    8/2011  Srivastava et al.
(Continued)

FOREIGN PATENT DOCUMENTS

WO          9614933          5/1996

OTHER PUBLICATIONS

Shao et al., Visual detection of multiple genetically modified organisms in a capillary array, Lab on a Chip, Issue 3, Royal Society of Chemistry 2017, 2 pages.
(Continued)

*Primary Examiner* — Lydia Edwards
(74) *Attorney, Agent, or Firm* — Thorpe North & Western LLP

(57) ABSTRACT

The present disclosure is drawn to microfluidic devices. In one example, a microfluidic device can include a first covered fluid feed slot in fluid communication with a first microfluidic channel and a second covered fluid feed slot in fluid communication with a second microfluidic channel. The first microfluidic channel can be formed adjacent to the second microfluidic channel but not in fluid communication with the second microfluidic channel. The first covered fluid feed slot can include a first fluid feed hole for filling a fluid into the first covered fluid feed slot. The second covered fluid feed slot can also include a second fluid feed hole for filling a fluid into the second covered fluid feed slot.

18 Claims, 10 Drawing Sheets

(52) U.S. Cl.
CPC ... *B01L 2200/147* (2013.01); *B01L 2300/088* (2013.01); *B01L 2300/0883* (2013.01); *B01L 2300/1827* (2013.01)

(58) Field of Classification Search
CPC ....... B01L 2300/1827; B01L 3/502723; B01L 3/502746; B01L 7/52; B01L 7/525; C12Q 1/68
See application file for complete search history.

(56) References Cited

U.S. PATENT DOCUMENTS

| | | |
|---|---|---|
| 9,404,881 B2 | 8/2016 | Glezer et al. |
| 9,555,408 B2 | 1/2017 | Tan et al. |
| 2002/0166592 A1 | 11/2002 | Liu et al. |
| 2002/0176804 A1 | 11/2002 | Strand et al. |
| 2015/0165438 A1 | 6/2015 | Taniguchi |
| 2016/0361715 A1 | 12/2016 | Shi et al. |

OTHER PUBLICATIONS

International Search Report dated Dec. 14, 2017 for PCT/US2017/026571, Applicant Hewlett-Packard Development Company, L.P.

MICROFLUIDIC DEVICES

BACKGROUND

Microfluidics relates to the behavior, control and manipulation of fluids that are geometrically constrained to a small, typically sub-millimeter, scale. Numerous applications employ passive fluid control techniques such as capillary forces. In some applications, external actuation techniques are employed for a directed transport of fluid. A variety of applications for microfluidics exist, with various applications using differing controls over fluid flow, mixing, temperature, evaporation, and so on.

BRIEF DESCRIPTION OF THE DRAWINGS

Additional features and advantages of the disclosure will be apparent from the detailed description which follows, taken in conjunction with the accompanying drawings, which together illustrate, by way of example, features of the present technology.

Figure 1:
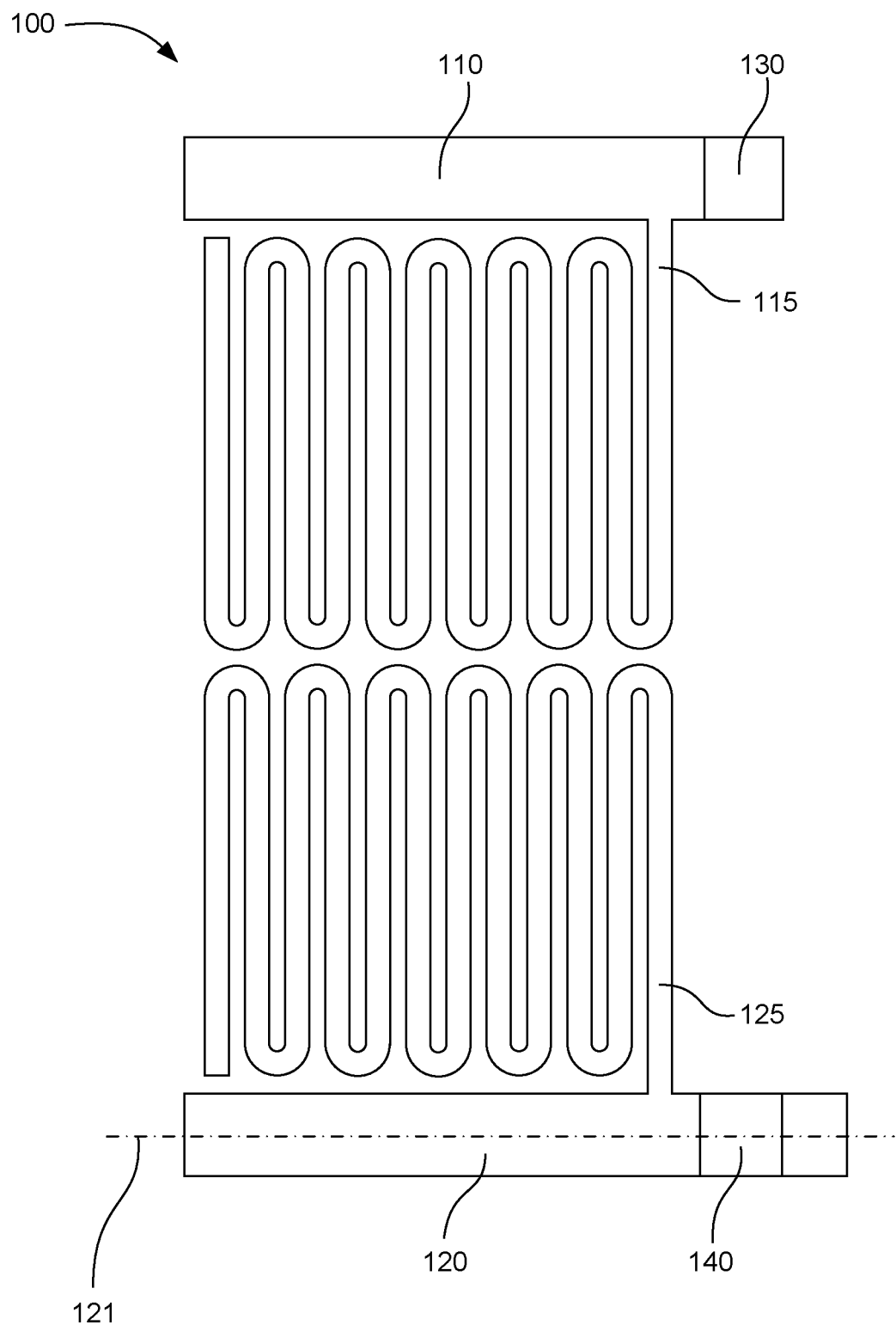
FIG. 1 is a schematic view of an example microfluidic device in accordance with the present disclosure.

Reference will now be made to several examples that are illustrated herein, and specific language will be used herein to describe the same. It will nevertheless be understood that no limitation of the scope of the disclosure is thereby intended.

DETAILED DESCRIPTION

The present disclosure is drawn to microfluidic devices. The microfluidic devices described herein can include a first covered fluid feed slot and a second covered fluid feed slot. The first covered fluid feed can be in fluid communication with a first microfluidic channel. Similarly, the second fluid feed slot can be in communication with a second microfluidic channel. The first and second microfluidic channels can be adjacent one to another but not in fluid communication one with another. The first and second covered fluid feed slots can each include a fluid feed hole for filling a fluid into the covered feed slots. In some examples, the fluid feed holes can have a smaller area than the first and second covered fluid feed slots.

In certain examples, the first microfluidic channel can be one of a first plurality of parallel microfluidic channels in fluid communication with the first covered fluid feed slot. The second microfluidic channel can also be one of a second plurality of parallel microfluidic channels in fluid communication with the second covered fluid feed slot.

In a further example, the first and second microfluidic channels can have a serpentine shape with a plurality of turns. In another example, the first and second microfluidic channels can be formed as loops connecting at both ends to the first and second covered fluid feed slots, respectively. In yet another example, the first and second microfluidic feed slots can be self priming by capillary force when a fluid is fed into the first and second fluid feed holes. Alternatively, in another example the device can include inertial pumps in the first and second microfluidic channels to pump fluid from the first and second covered fluid feed slots into the first and second microfluidic channels, respectively.

In certain examples, the device can include first and second vent chambers in fluid communication with the first and second microfluidic channels. The vent chambers can be connected to the microfluidic channels through first and second capillary breaks. The capillary breaks can include tapered portions and narrowed openings with a smaller width than a width of the first and second microfluidic channels. Additionally, the device can include first and second vent ports to vent gas from the first and second vent chambers. The vent ports can be located a distance away from the first and second capillary breaks such that fluid in the capillary breaks does not escape through the first and second vent ports. In a particular example, the device can include a first plurality of microfluidic channels connecting the first covered fluid feed slot to the first vent chamber through capillary breaks, and a second plurality of microfluidic channels connecting the second covered fluid feed slot to the second vent chamber through capillary breaks. In one example, the first plurality of microfluidic channels and the second plurality of microfluidic channels can be interdigitated in an area between the first covered fluid feed and the second covered fluid feed slot.

The present technology also extends to microfluidic nucleic acid testing devices. In one example, a microfluidic nucleic acid testing device can include a first covered fluid feed slot and a second covered fluid feed slot. The first covered fluid feed slot can be in fluid communication with a first microfluidic channel. Similarly, the second covered fluid feed slot can be in communication with a second microfluidic channel. One or more heating resistors can be located proximate to the first and second microfluidic channels, so that the heating resistors can heat a fluid in the microfluidic channels. The first microfluidic channel can be formed adjacent to the second microfluidic channel but not in fluid communication with the second microfluidic channel. Additionally, the first covered fluid feed slot can include a first fluid feed hole for filling a fluid into the first covered fluid feed slot. In some examples, the first fluid feed hole can have a smaller area than the first covered fluid feed slot. Similarly, the second covered fluid feed slot can include a second fluid feed hole for filling a fluid into the second covered fluid feed slot. In some examples, the second fluid feed hole can have a smaller area than the second covered fluid feed slot.

In a further example, the microfluidic nucleic acid testing device can include first and second vent chambers in fluid communication with the first and second microfluidic channels through first and second capillary breaks. The first and second capillary breaks can include tapered portions and narrow openings with smaller widths than a width of the first and second microfluidic channels. The microfluidic nucleic acid testing device can also include first and second vent ports to vent gas from the first and second vent chambers.

The first and second vent ports can be located a distance away from the first and second capillary breaks such that fluid in the capillary breaks does not escape through the first and second vent ports.

In another example, a microfluidic nucleic acid testing device can also include one or more temperature sensors located proximate to the first and second microfluidic channels. The temperature sensors can measure a temperature of a fluid in the microfluidic channels.

In a particular example, the first and second microfluidic channels can be formed as loops connecting at both ends to the first and second covered fluid feed slots, respectively. The microfluidic nucleic acid testing device can also include inertial pumps in the first and second microfluidic channels to circulate fluid through the first and second microfluidic channels.

In yet another example, a microfluidic device can include a first covered fluid feed slot including a first fluid feed hole for filling a fluid into the first covered fluid feed slot. In some examples, the first fluid feed hole can have a smaller area than the first covered fluid feed slot. The microfluidic device can also include a second covered fluid feet slot oriented parallel to the first covered fluid feed slot. The second covered fluid feed slot can include a second fluid feed hole for filling a fluid into the second covered fluid feed slot. In some examples, the second fluid feed hole can have a smaller area than the second covered fluid feed slot. A first series of microfluidic channel bundles can connect to the first covered fluid feed slot. A second series of microfluidic channel bundles can connect to the second covered fluid feed slot. The first and second series of microfluidic channel bundles can be interdigitated in an area between the first and second covered fluid feed slots.

In a further example, the microfluidic channel bundles can each include a plurality of microfluidic channels connected to a vent chamber through capillary breaks. The capillary breaks can include tapered portions and narrowed openings with a smaller width than a width of the microfluidic channels. The vent chamber can be in communication with a vent port to vent gas from the vent chamber.

The microfluidic devices described herein can provide reduced evaporation of fluid in microfluidic channels, eliminate air bubbles trapped in the microfluidic channels, and improve priming of the microfluidic channels in the microfluidic devices. These devices can also allow for parallel processing of multiple fluids in close proximity. In some applications, this can be useful for performing multiplex assays and/or comparing a test fluid with a control fluid. Nucleic acid testing is one example of an area in which these features can be useful. Nucleic acid tests, such as nucleic acid amplification tests, polymerase chain reaction (PCR) tests, and other nucleic acid tests, are often performed with small volumes of sample fluid. Thus, the microfluidic devices described herein, with their small internal fluid volumes, can be useful for testing these small sample volumes. The reduced evaporation provided by the microfluidic devices can be especially useful to ensure that the sample does not evaporate too quickly before a test can be completed. Additionally, some types of nucleic acid tests involve heating the sample fluid to elevated temperatures. If air bubbles are present in the microfluidic channels, then the heating can cause the air bubble to expand, potentially blowing out the sample fluid from the microfluidic channels or even damaging the microfluidic device. The devices described herein can reduce the occurrence of air bubbles in the microfluidic channels. This can make the devices more reliable for many applications, and especially for applications involving heating of the sample fluid.

In further examples, the microfluidic devices described herein can be used for testing a variety of bio-chemical targets. The adjacent microfluidic channels can generally be used to test a sample in one of the microfluidic channels and a reference reaction in the adjacent microfluidic channel. For example, a sample fluid to be tested for a target compound can be reacted with reagents in one microfluidic channel while a control fluid, or "placebo" that is known not to contain the target compound, can be mixed with the same reagents in the adjacent microfluidic channel. The reactions occurring in each microfluidic channel can be compared to determine whether the sample fluid contains the target. For example, if the sample fluid contains the target compound then the first microfluidic channel can produce a positive signal while the adjacent microfluidic with the control fluid produces no signal. This can reduce signal-to-noise ratio in the test and increase the test sensitivity. In another example, the sample fluid can be compared to a reference fluid that has a known concentration of the target compound. In some examples, the device can have multiple microfluidic channels that can be loaded with multiple test samples, control fluids containing no target compound, and reference fluids containing a known concentration of target compound. This can provide a robust test with reduced likelihood of false positives and false negatives.

Non-limiting examples of tests that can be performed using the microfluidic devices described herein can include enzyme-linked immunoabsorbent assay (ELISA) immunoassay testing, nucleic acid amplification testing (NAAT) using polymerase chain reaction (PCR), isothermal amplification such as multiple displacement amplification (MDA), loop-mediated isothermal amplification (LAMP), rolling circle amplification (RCA), helicase-dependent amplification (HAD), recombinase polymerase amplification (RPA), nucleic acid sequence-based amplification (NASBA), hematology testing, and so on. A variety of other biochemical and non-biochemical tests can also benefit from the reduced evaporation and enhance priming of the microfluidic channels provided by the microfluidic devices described herein.

FIG. 1 shows an example of a microfluidic device 100 according to the present technology. The device can include a first covered fluid feed slot 110 in communication with a first microfluidic channel 115, and a second covered fluid feed slot 120 in communication with a second microfluidic channel 125. The first microfluidic channel can be formed adjacent to the second microfluidic channel but not in fluid communication with the second microfluidic channel. The first covered fluid feed slot can include a first fluid feed hole 130. The first fluid feed hole can have a smaller area than the first covered fluid feed slot, as viewed from above. Similarly, the second covered fluid feed slot can have a second fluid feed hole 140. The second fluid feed hole can have a smaller area than the second covered fluid feed slot, as viewed from above.

The microfluidic device can include a substrate (not shown in FIG. 1, but shown at 150 in FIG. 2) on top of which the covered fluid feed slots and microfluidic channels are located. In some examples, the fluid feed holes can be openings in the substrate. Fluid can be introduced into the covered fluid feed slots from beneath the device using these openings in the substrate. A majority of the covered fluid feed slot can be covered from below by the substrate. Thus, in some examples the amount of evaporation occurring through the substrate can be reduced because evaporation only occurs through the smaller fluid feed holes.

The microfluidic device can also include a top layer (not shown in FIG. 1, but shown at 165 in FIG. 2) that covers the microfluidic channels and the covered fluid feed slots from above. In further examples, the fluid feed holes can be an opening in this top layer, allowing fluid to be filled into the covered fluid feed slots. Because the majority of the covered fluid feed slot can be covered by the top layer, evaporation from the covered fluid feed slot can only occur through the fluid feed hole. Thus, using a fluid feed hole with a smaller area than the covered fluid feed slot can greatly reduce the amount of evaporation compared to a fluid feed slot that is open on the top. Accordingly, fluid feed holes can be formed in the top layer and/or in the substrate, with the top layer and substrate covering the covered fluid feed slots above and below, respectively. In particular, in some examples the entire area of the covered fluid feed slots can be covered above and below with the exception of the fluid feed holes.

Although the example fluid feed holes have been described above as having an area smaller than the area of the covered fluid feed slots, in some examples the fluid feed holes can have the same area as the covered fluid feed slots. In other words, in some examples the entire covered fluid feed slot can be open through either the substrate or the top layer. In certain examples, the microfluidic device can be a part of a larger system that includes a fluid delivery system to deliver fluid to the fluid feed holes. In such examples, the fluid delivery system can form a seal with the fluid feed holes so that evaporation at the fluid feed holes may not be an issue. In further examples, the fluid delivery system can be designed to reduce evaporation elsewhere in the fluid delivery system. In still further examples, smaller fluid feed holes can be used even when used together with such a sealed fluid delivery system. Although the smaller fluid feed holes may not affect evaporation in such examples, the smaller fluid feed holes can also provide the advantage of uniformly and sequentially priming microfluidic channels along the covered fluid feed slots. In such examples, fluid can enter the covered fluid feed slot at the fluid feed hole. The fluid can then flow along the covered fluid feed slot, sequentially priming each microfluidic channel as the fluid reaches the channels.

Figure 2:
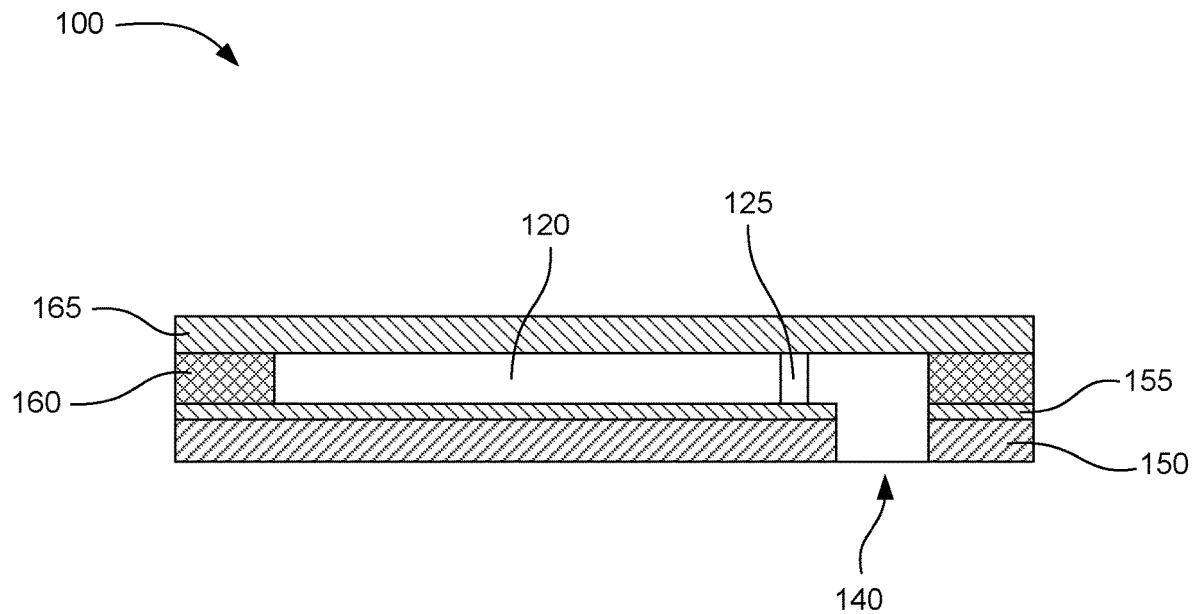
FIG. 2 is a side cross-sectional view of the example microfluidic device of FIG. 1.

To clarify the structure of the microfluidic devices described herein, FIG. 2 shows a side cross sectional view of the example device 100 shown in FIG. 1, viewing the device as cut along plane 121 through the center of the second covered fluid feed slot. In this particular example, the device can be formed with a substrate 150, a primer layer 155, a microfluidic layer 160 defining the walls of the covered fluid feed slots and microfluidic channels, and a top layer 165 covering the microfluidic layer. The second fluid feed hole 140 can be an opening through the substrate and primer layer. FIG. 2 shows the second covered fluid feed slot 120 covered by the top layer. An opening in the side wall of the second covered fluid feed slot can lead to the second microfluidic channel 125.

The microfluidic devices described are not limited to being formed by any particular process. However, in some examples, any of the microfluidic devices described herein can be formed from multiple layers as shown in FIG. 2. In certain examples, the one or more of the layers can be formed photolithographically using a photoresist. In one such example, the layers can be formed from an epoxy-based photoresist such as SU-8 or SU-8 2000 photoresist, which are epoxy-based negative photoresists. Specifically, SU-8 and SU-8 200 are Bisphenol A Novolac epoxy-based photoresists that are available from various sources, including MicroChem Corp. These materials can be exposed to UV light to become crosslinked, while portions that are unexposed remain soluble in a solvent and can be washed away to leave voids.

In some examples, the substrate can be formed of a silicon material. For example, the substrate can be formed of single crystalline silicon, polycrystalline silicon, gallium arsenide, glass, silica, ceramics or a semiconducting material. In a particular example, the substrate can have a thickness from about 500 µm to about 1200 µm. In certain examples, the fluid feed holes can be formed in the silicon substrate by laser machining and/or chemical etching.

In further examples, the primer layer can be a layer of a photoresist material, such as SU-8, with a thickness from about 2 µm to about 100 µm.

The microfluidic layer 160 can be formed by exposing a layer of photoresist with a pattern of walls to define the covered fluid feed slots and microfluidic channels, and then washing away the unexposed photoresist. In some examples, the microfluidic layer can have a thickness from about 2 µm to 100 µm. The microfluidic channels can be formed having a width from about 2 µm to about 100 µm, from about 10 µm to about 50 µm, or from about 20 µm to about 30 µm.

In certain examples, the top layer 165 can be formed by laminating a dry film photoresist over the microfluidic layer and exposing the dry film photoresist with a UV pattern defining the fluid feed holes. In other examples, the fluid feed holes can be openings in the substrate, and the top layer can be substantially solid without any openings for fluid feed holes. The top layer can have a thickness from about 2 µm to about 200 µm.

In some examples, the microfluidic channels can have a serpentine shape, as shown in FIG. 1. The serpentine channels can have multiple turns to allow a great length of microfluidic channel to occupy a small area. In some cases, the turns can be rounded as shown in FIG. 1. In other examples, the turns can have sharp angles such as 90° angles, 45° angles, and so on.

Figure 3:
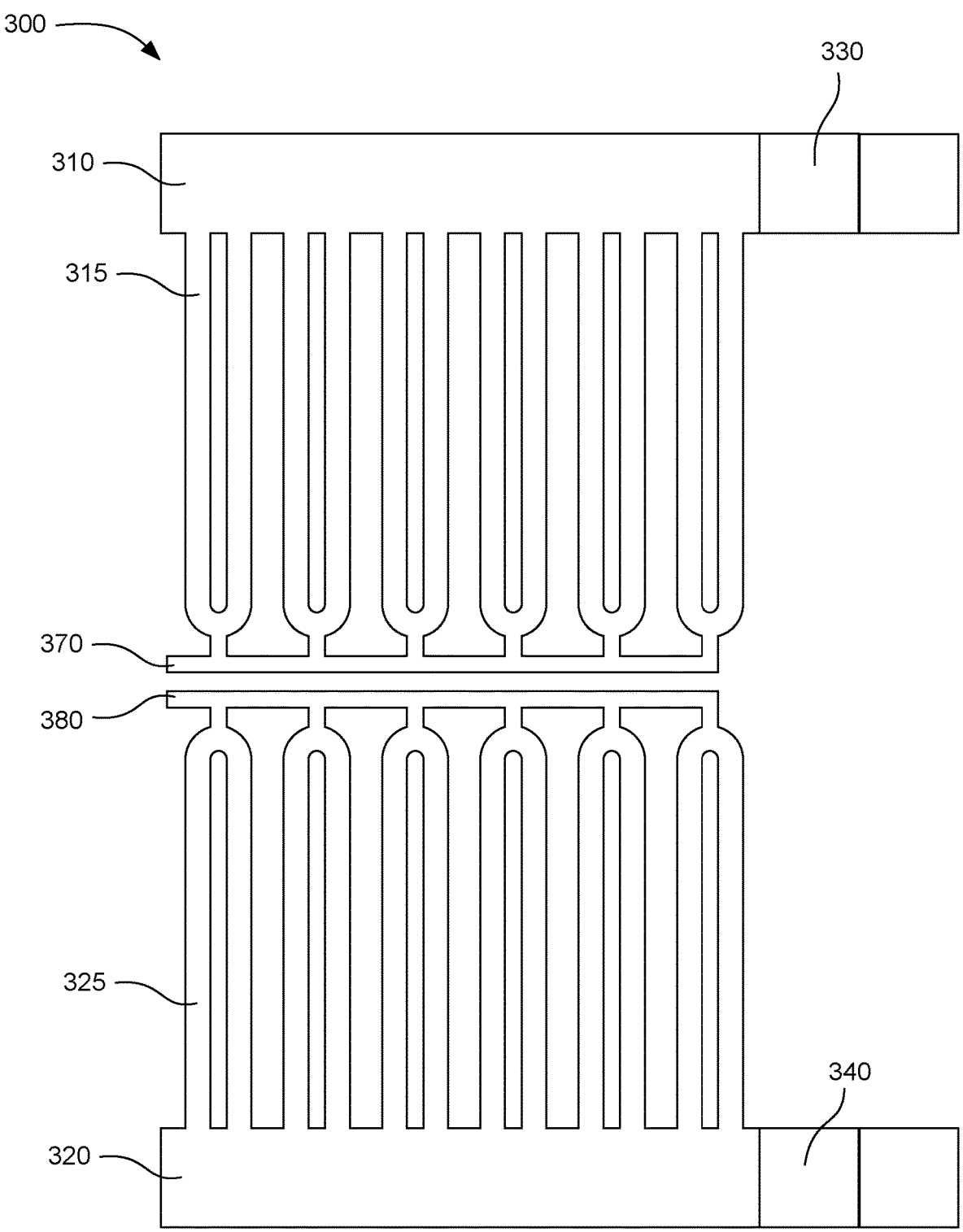
FIG. 3 is a schematic view of an example microfluidic device in accordance with the present disclosure.

Microfluidic devices according to the present technology can also have other layouts. FIG. 3 shows another example microfluidic device 300 having a first covered fluid feed slot 310, a second covered fluid feed slot 320, a first fluid feed hole 330, and a second fluid feed hole 340. This design can include a first plurality of microfluidic channels 315 formed as loops connecting to the first covered fluid feed slot at both ends. A second plurality of microfluidic channels 325 can be in the form of loops connecting to the second covered fluid feed slot at both ends. The first and second pluralities of microfluidic channels can also be connected to first and second vent chambers 370, 380.

Figure 4:
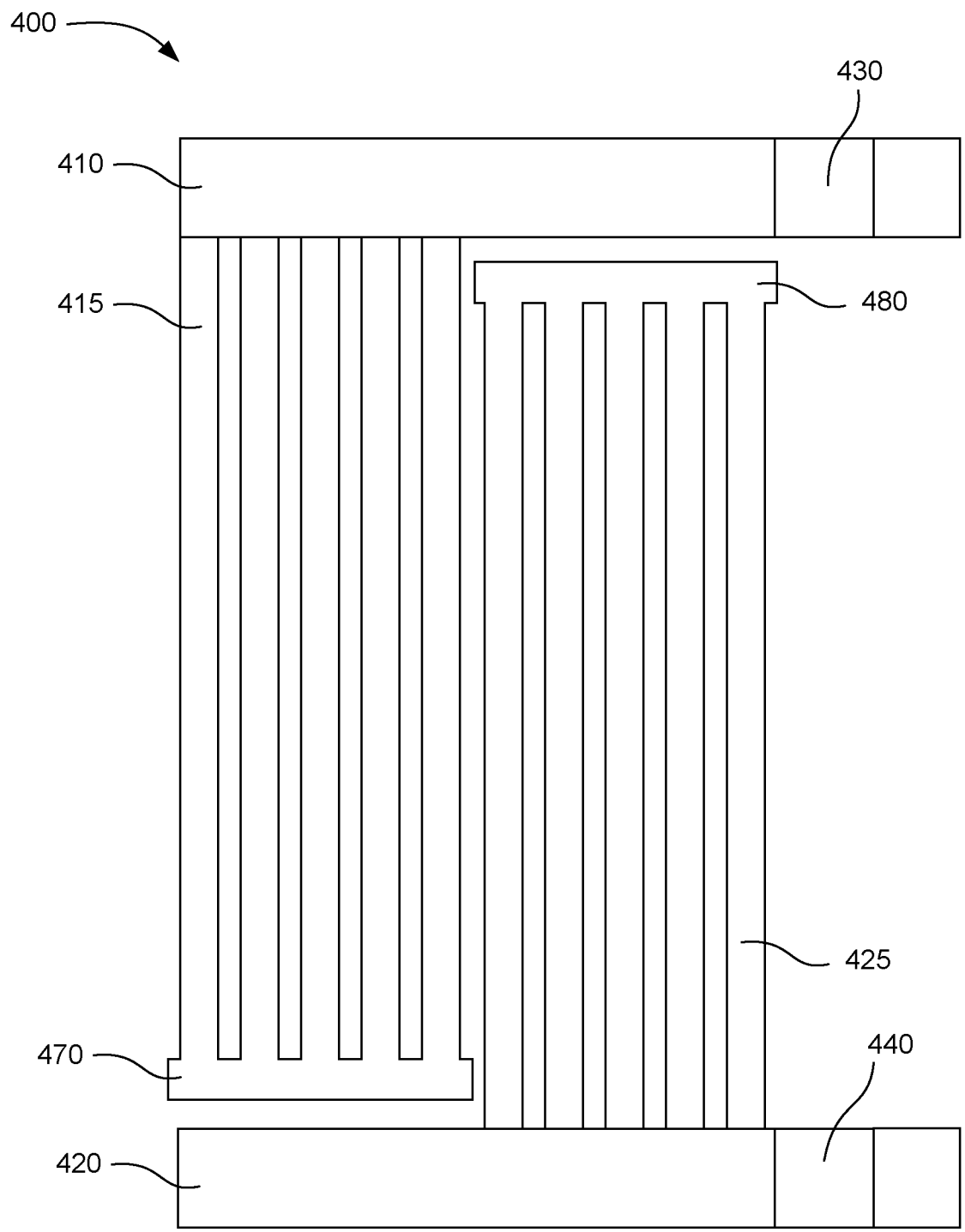
FIG. 4 is a schematic view of an example microfluidic device in accordance with the present disclosure.

Another example microfluidic device 400 is shown in FIG. 4. This device can include a first covered fluid feed slot 410 with a first fluid feed hole 430 and a second covered fluid feed slot 420 with a second fluid feed hole 440. A first plurality of parallel microfluidic channels 415 can be connected to the first covered fluid feed slot. A second plurality of parallel microfluidic channels 425 can be connected to the second covered fluid feed slot. The first and second pluralities of microfluidic channels can lead to first and second vent chambers 470, 480.

In further examples of the present technology, the microfluidic channels can lead to vent chambers that are in fluid connection with vent ports. The vent ports can facilitate priming of the microfluidic channels by allowing air in the microfluidic channels to escape when fluid enters the microfluidic channels. In various examples, the size and number of vent ports can be minimized to reduce evaporation of fluid through the vent ports.

In certain examples, the vent port can have a width smaller than a width of the microfluidic channels. For example, the vent port can have a width from 1 μm to 50 μm, 2 μm to 30 μm, or 5 μm to 20 μm in some cases. In further examples, the vent port can have a width that is from 1% to 99% the width of the microfluidic channels, 5% to 50% the width of the microfluidic channels, or 5% to 25% the width of the microfluidic channels. The shape of the vent port is not particularly limited. In some examples, the vent port can be circular, square, rectangular, or another shape.

The number of vent ports included in a microfluidic device can be reduced by connecting multiple microfluidic channels to a single vent chamber with a single vent port. In this way, a number of microfluidic channels full of fluid can be primed, allowing the air in the microfluidic channels to escape through the vent port. Then, evaporation in the microfluidic channels can be reduced because only the single vent port is available as a path for evaporation. Such a microfluidic device can have reduced evaporation compared to a device in which each microfluidic channel has its own vent port.

In another example, the number of vent ports can be reduced by using a vent port at the end of a long microfluidic channel. As mentioned above, using a serpentine shaped microfluidic channel with a plurality of turns can allow a long microfluidic channel to occupy a small area. In one example, a single vent port can be formed at the end of a long serpentine microfluidic channel.

In some cases, using lamination of a dry photoresist layer to form the top layer of the device can allow for the use of a single vent port with multiple microfluidic channels, or very long microfluidic channels as described above. Some other methods of forming the top layer, such as using a lost wax method, can require additional ports in the top layer. For example, in a lost wax method, the microfluidic channels can be filled with a wax before applying the top layer. The wax can then be removed from the microfluidic channels. However, in some cases wax can be removed only up to a finite distance away from a port. Therefore, multiple ports in the top layer may be used so that all of the wax can be removed. However, these ports can also increase the amount of fluid evaporation when the device is in use. By laminating a dry photoresist layer as the top layer, the requirement of removing wax from the microfluidic channels can be eliminated. Therefore, a single vent port can be used at the end of a long microfluidic channel or multiple microfluidic channels can be connected to a single vent port.

In further examples, a ratio of the number of vent ports in the microfluidic device to the total volume of fluid in the microfluidic channels can be from 1 vent port per 1 nL to 1 vent port per 100 nL. In certain examples, the microfluidic device can have as few as one vent per covered fluid feed slot.

The microfluidic devices according to the present technology can also include capillary breaks between the microfluidic channels and the vent chambers to stop fluid in the microfluidic channels from reaching the vent ports. As used herein, a "capillary break" refers to a microfluidic structure that includes a tapered portion and a narrow opening, in which the capillary force holding fluid in the narrow opening is increased with respect to the capillary force in the microfluidic channels. Thus, the capillary breaks can taper to a narrow opening that has a smaller width than the width of the microfluidic channel.

Figure 5:
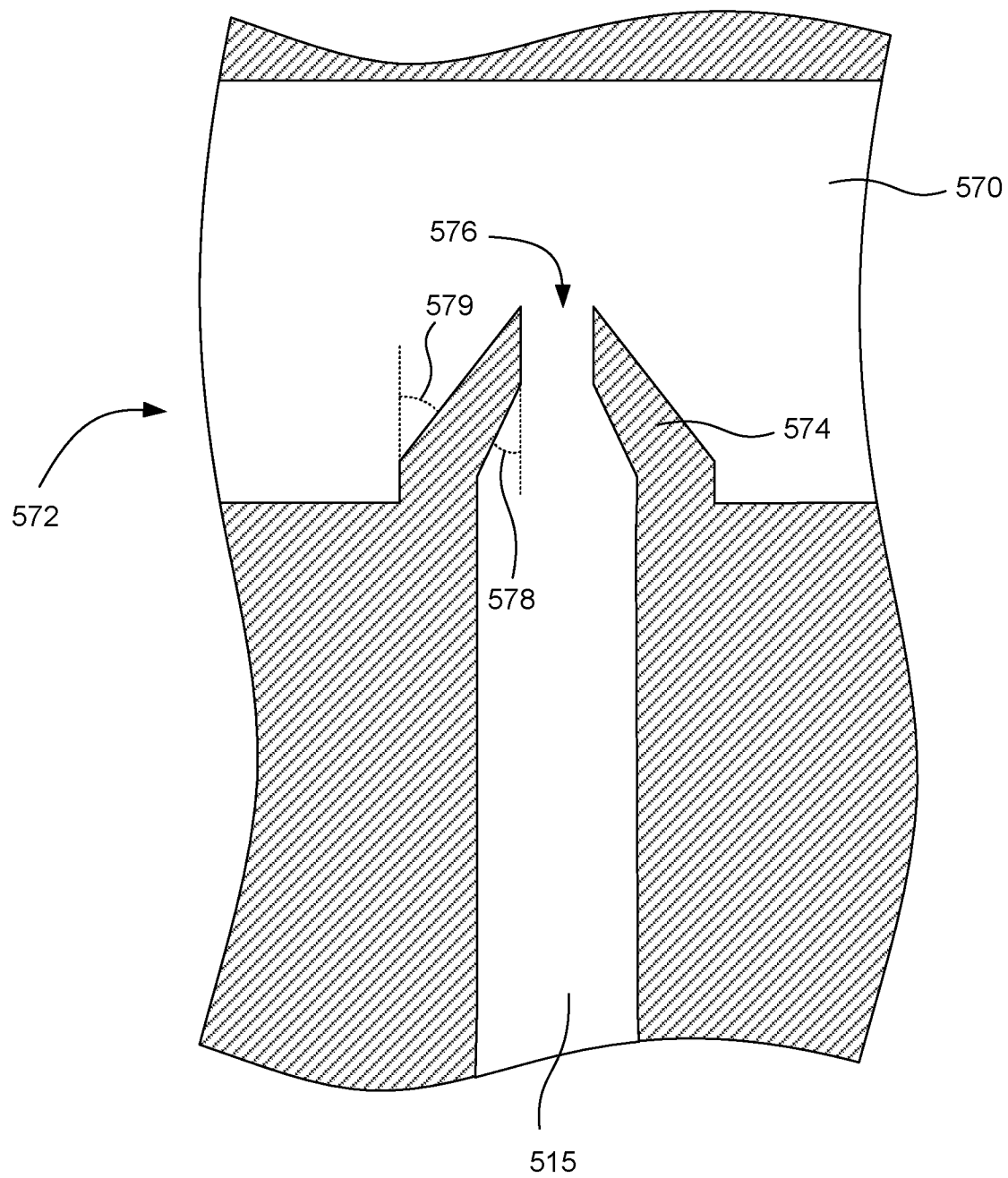
FIG. 5 is a top cross-sectional view of a capillary break in accordance with the present disclosure.

FIG. 5 shows one example of a capillary break 572 that can be used in the present microfluidic devices. The capillary break can include a tapered portion 574 and a narrow opening 576. In this example, the capillary break can begin at the width of the microfluidic channel 515 and taper to the narrow opening. The narrow opening can extend into the vent chamber 570. When the microfluidic channel is primed with fluid, the fluid can flow into the narrow opening of the capillary break and form a meniscus. The narrow opening can have a smaller width than the microfluidic channel, and also a smaller width compared to the interior of the vent chamber. This can cause the capillary force to be greatest in the narrow opening, which can tend to retain the fluid in the narrow opening. The amount of force necessary to break the meniscus and force fluid to flow through the capillary break can also be increased by using a sharp angle between the narrow opening and the exterior tapered portion in the vent chamber. In this example, the interior tapering angle 578 and exterior tapering angle 579 are shown in dashed lines. In some examples, the interior tapering angle and exterior tapering angle can independently be from about 5° to about 45°. In further examples, the narrow opening can have a width that is from 1% to 90% the width of the microfluidic channel. In more specific examples, the narrow opening can have a width that is from 2% to 60% or from 5% to 40% the width of the microfluidic channel. In one example, the narrow opening can have a width from about 1 μm to about 30 μm. In another example, the narrow opening can have a width from about 2 μm to about 16 μm.

Figure 6:
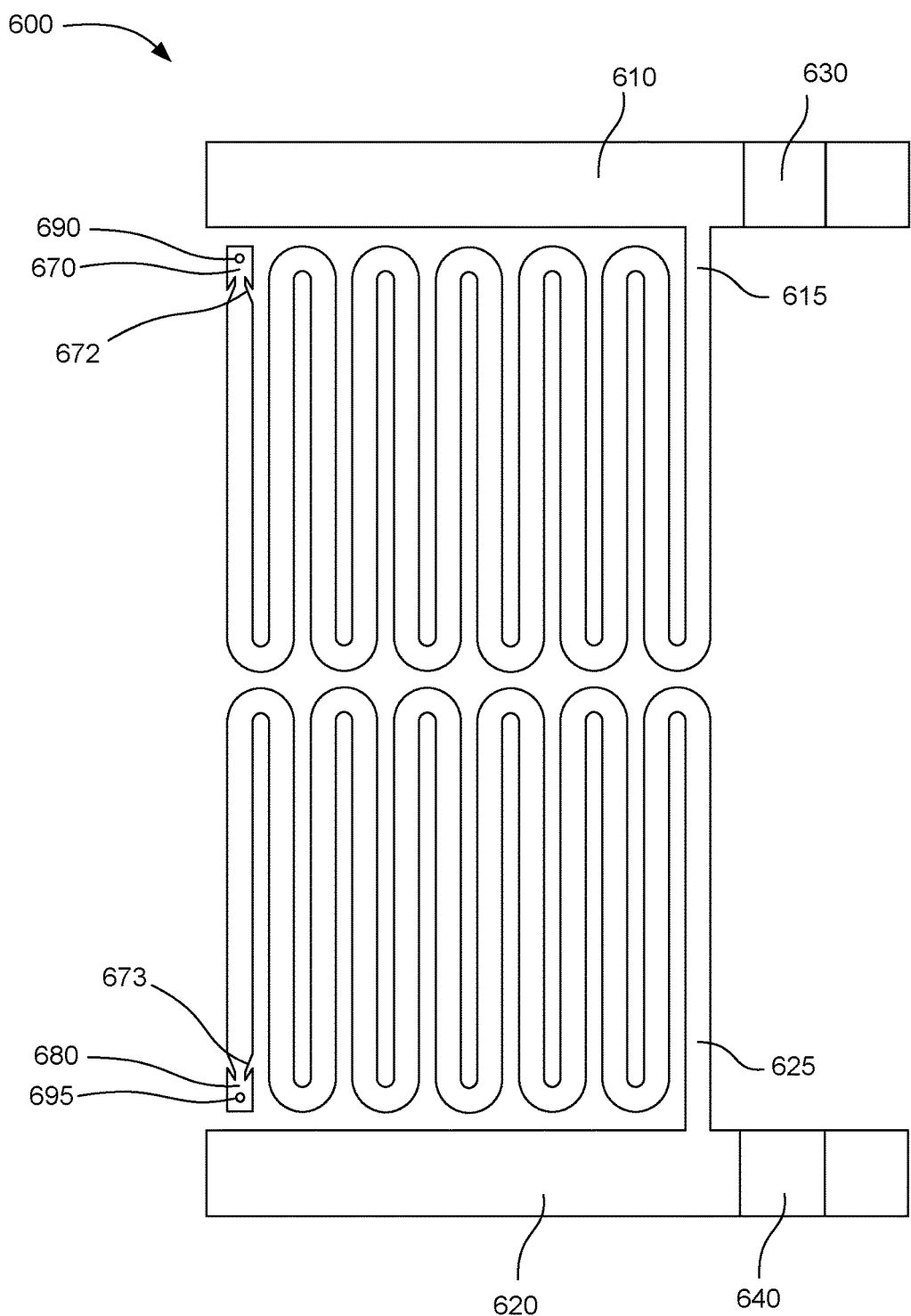
FIG. 6 is a schematic view of an example microfluidic device in accordance with the present disclosure.

Capillary breaks can be incorporated with vent chambers and vent ports to allow for improved priming of the microfluidic channels. FIG. 6 shows an example of a microfluidic device 600 that includes a first covered fluid feed slot 610, a second covered fluid feed slot 620, a first fluid feed hole 630, a second fluid feed hole 640, a first microfluidic channel 615, and a second microfluidic channel 625. The first and second microfluidic channels can lead to first and second capillary breaks 672, 673. The capillary breaks can prevent fluid from entering first and second vent chambers 670, 680 and escaping through first and second vent ports 690, 695.

Figure 7:
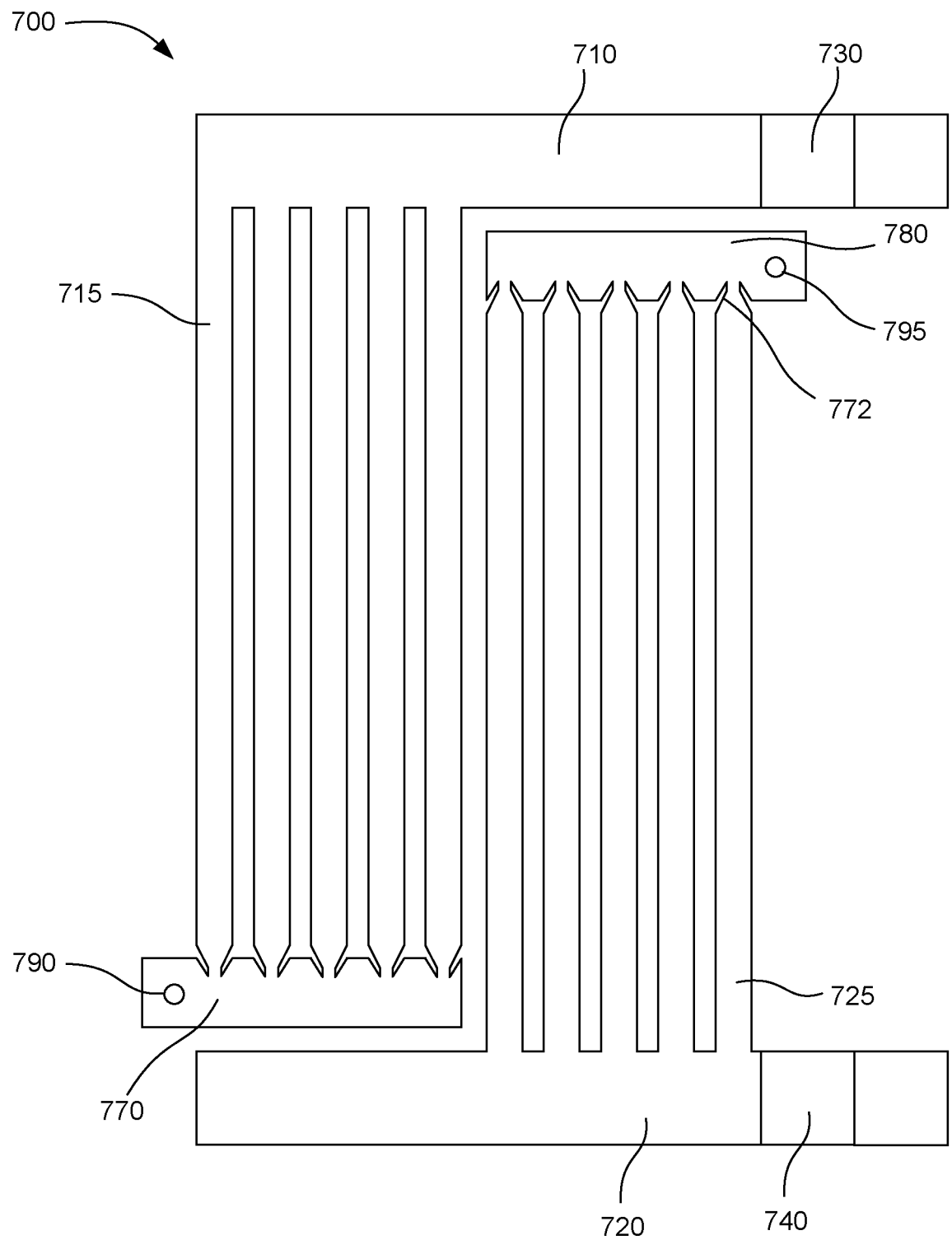
FIG. 7 is a schematic view of an example microfluidic device in accordance with the present disclosure.

FIG. 7 shows another example of a microfluidic device 700. This device can include first and second covered fluid feed slots 710, 720 with first and second fluid feed holes 730, 740. The covered fluid feed slots can be connected to first and second pluralities of parallel microfluidic channels 715, 725. Each microfluidic channel can lead to a capillary break 772, which separates the microfluidic channels from first and second vent chambers 770, 780. The capillary breaks can prevent fluid from escaping through first and second vent ports 790, 795.

In some examples, a microfluidic device can be designed to move fluid through the microfluidic channels solely by capillary force. For example, the covered fluid feed slots and microfluidic channels can be designed so that the microfluidic channels are self priming by capillary force. In one example, a microfluidic channel can have a sufficiently small width that the fluid is drawn into the microfluidic channel by capillary force. The microfluidic channel can be connected to a vent chamber and vent port through a capillary break as explained above, so that the air displaced by the fluid can escape through the vent port, but the fluid will stop at the capillary break.

However, in other examples, the microfluidic device can include inertial pumps to actively move fluids through the microfluidic channels. An inertial pump can include a fluid actuator such as a piezoelectric element or a thermal resistor. The fluid actuator can displace fluid by moving a piezoelectric element or boiling the fluid to form a bubble. The fluid actuator can be placed in a microfluidic channel in a location that is asymmetric with respect to the length of the microfluidic channel. When the fluid actuator repeatedly displaces fluid, a net flow can be produced in one direction. For example, the fluid actuator can be placed close to the connection between the microfluidic channel and the covered fluid feed slot to produce a net flow of fluid out of the covered fluid feed slot and into the microfluidic channel.

Figure 8:
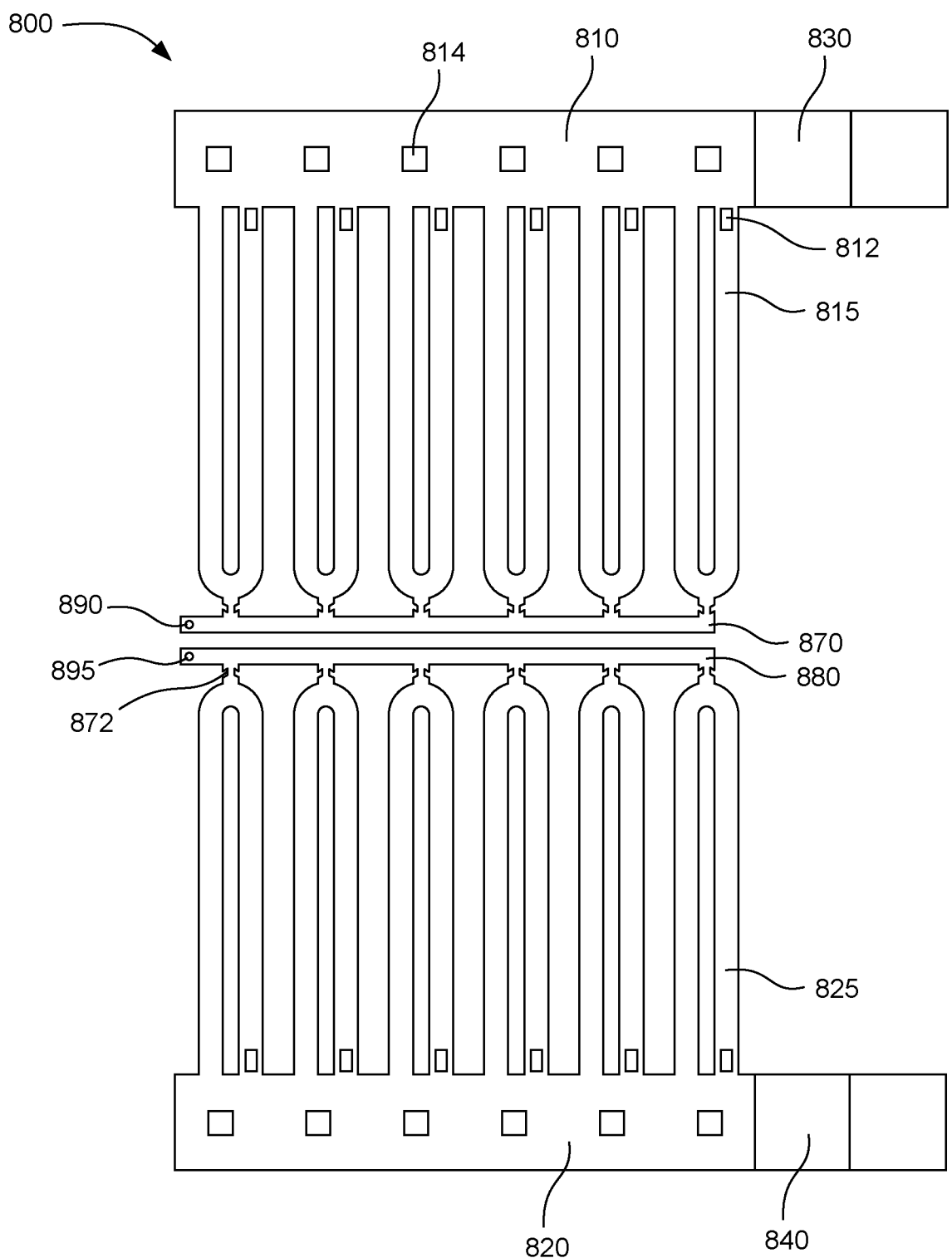
FIG. 8 is a schematic view of an example microfluidic device in accordance with the present disclosure.

FIG. 8 shows another example of a microfluidic device 800. The device can include first and second covered fluid feed slots 810, 820 with first and second fluid feed holes 830, 840. A first plurality of microfluidic channels 815 can be formed as loops connecting to the first covered fluid feed slot at both ends. A second plurality of microfluidic channels 825 can also be formed as loops connecting to the second covered fluid feed slot at both ends. The microfluidic channels can also be connected to first and second vent chambers 870, 880 through capillary breaks 872. The vent chambers can be in fluid communication with first and second vent ports 890, 895.

The example shown in FIG. 8 also includes resistors 812 in the microfluidic channels. The resistors can form bubbles to displace fluid in the microfluidic channels. Because the resistors can be located asymmetrically with respect to the length of the microfluidic channels, the resistors can create a net fluid flow in one direction and act as inertial pumps. In this example, the resistors can circulate fluid through the loops of the microfluidic channels.

The example shown in FIG. 8 can also include pillars 814 formed in the covered fluid feed slots 810, 820. These pillars can be formed of solid material as a part of the microfluidic layer. The pillars can provide additional support for the top layer over the covered fluid feed slots. When the top layer is formed by laminating a dry photoresist layer instead of using a lost wax method, the pillars can help support the dry photoresist layer during lamination to prevent sagging or breakage of the top layer.

In further examples, any of the designs described above can be adapted for various lengths of covered fluid feed slots. For example, a much longer covered fluid feed slot can be used with multiples of the microfluidic channel designs connected along the length of the covered fluid feed slot. In such examples, a single fluid feed hole can be located at one end of the long covered fluid feed slot. Alternatively, two fluid feed holes can be used, one at each end of the long covered fluid feed slot. Additional fluid feed holes can optionally be added along the length of the covered fluid feed slot if desired.

Figure 9:
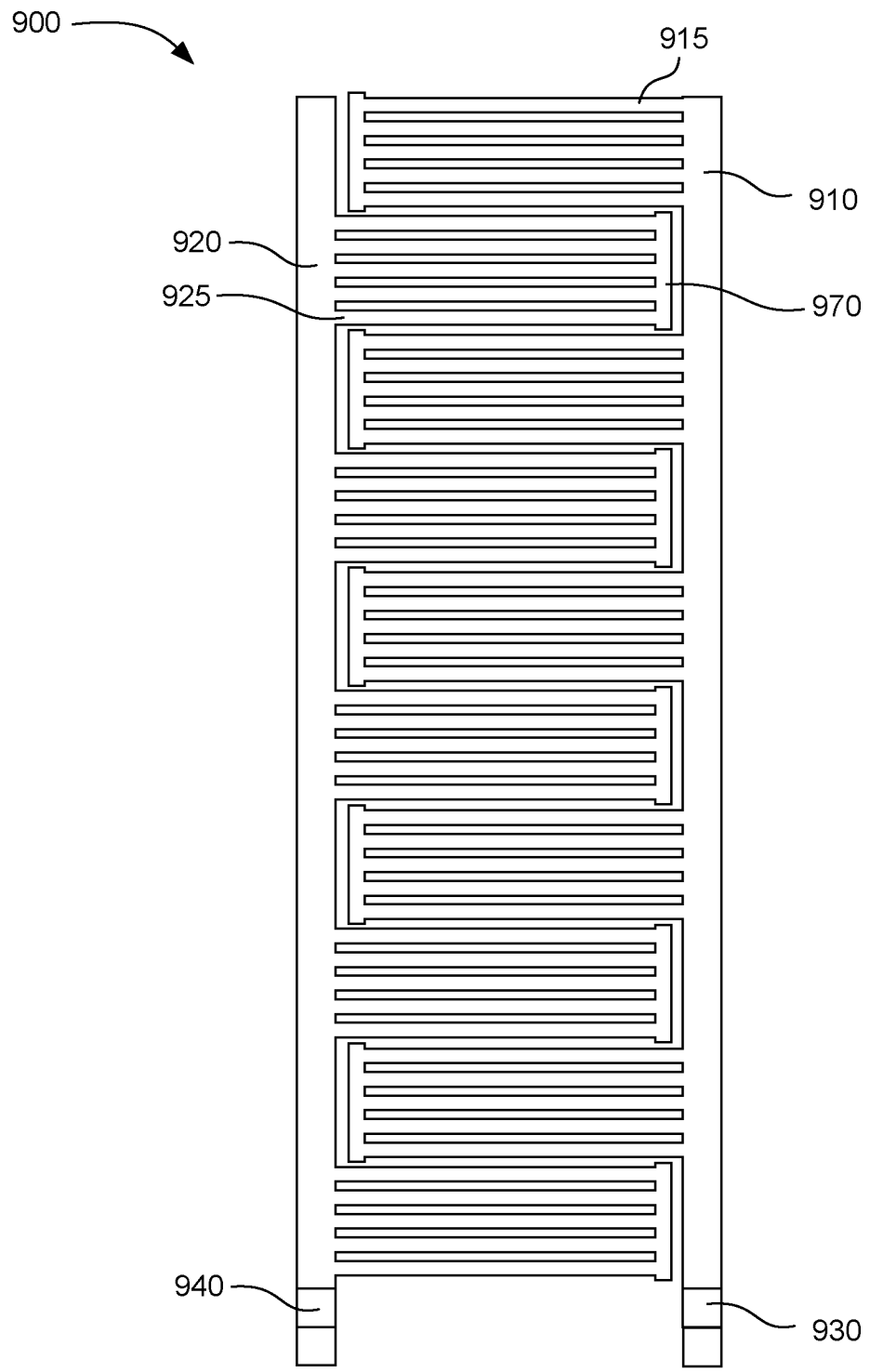
FIG. 9 is a schematic view of an example microfluidic device in accordance with the present disclosure.

FIG. 9 shows an example of a microfluidic device 900 with longer first and second covered fluid feed slots 910, 920. The first and second covered fluid feed slots can be filled by first and second fluid feed holes 930, 940. Each of the covered fluid feed slots can be connected to a plurality of microfluidic channels, organized into a first series of microfluidic channel bundles 915 and a second series of microfluidic channel bundles 925. The microfluidic channel bundles can connect to vent chambers 970. The first series of microfluidic channel bundles and the second series of microfluidic channel bundles can be interdigitated in an area between the first and second covered fluid feed slots. Although not shown in FIG. 9, this example can incorporate other design features described above such as capillary breaks and vent ports.

In various examples, the covered fluid feed slots can range in length from about 100 μm to 50,000 μm or longer. In further examples, the covered fluid feed slots can have widths ranging from 30 μm to 1,000 μm. Shorter covered fluid feed slots can connect to one or a few microfluidic channels. Longer covered fluid feed slots can connect to many more microfluidic channels. In some cases, using a longer covered fluid feed slot with a single fluid feed hole can improve evaporation because only a small amount of fluid evaporates from the single fluid feed hole relative to the larger volume of fluid in the covered fluid feed slot and connecting microfluidic channels. In certain examples, the ratio of the area of the fluid feed hole to the area of the covered fluid feed slot can range from 1:10 to 1:10,000. In further examples, the fluid feed holes can have a length from about 20 μm to about 10,000 μm, and a width from about 20 μm to about 1,000 μm. In more specific examples, the fluid feed holes can have a length from about 20 μm to about 110 μm. The fluid feed holes can also be formed with a variety of shapes, such as square, rectangular, or circular.

Figure 10:
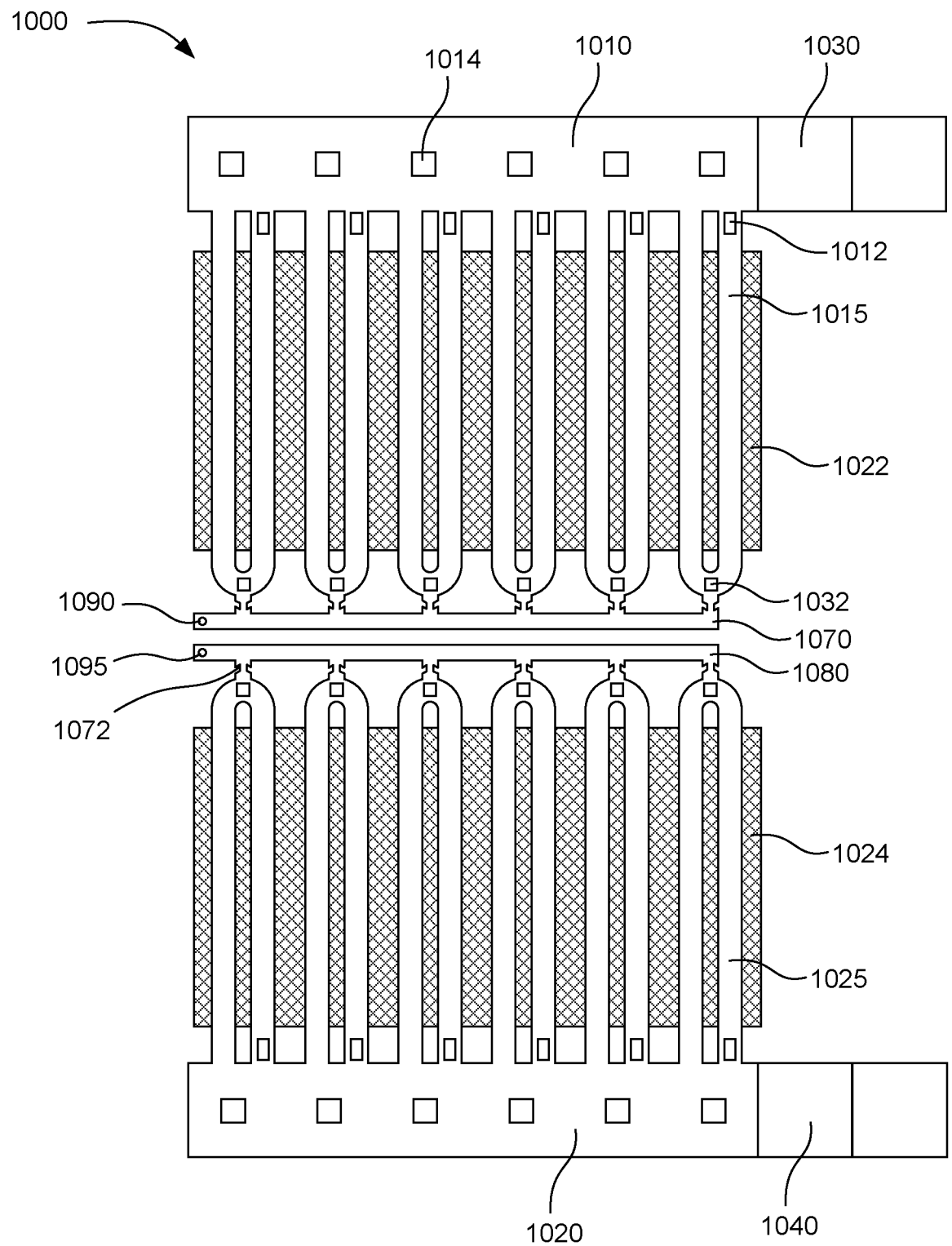
FIG. 10 is a schematic view of an example microfluidic nucleic acid testing device in accordance with the present disclosure.

The microfluidic devices described herein can be used for a variety of applications. In certain examples, the microfluidic devices can be nucleic acid testing devices. FIG. 10 shows an example of a microfluidic nucleic acid testing device 1000. The device can include first and second covered fluid feed slots 1010, 1020 with first and second fluid feed holes 1030, 1040. The covered fluid feed slots can include pillars 1014 to support the top layer. A first plurality of microfluidic channels 1015 can be formed as loops connecting to the first covered fluid feed slot at both ends. A second plurality of microfluidic channels 1025 can also be formed as loops connecting to the second covered fluid feed slot at both ends. The microfluidic channels can include resistors 1012 to act as inertial pumps to circulate fluid through the loops. The microfluidic channels can also be connected to first and second vent chambers 1070, 1080 through capillary breaks 1072. The vent chambers can be in fluid communication with first and second vent ports 1090, 1095 to allow air to escape during priming of the microfluidic channels.

The microfluidic nucleic acid testing device shown in FIG. 10 can also include first and second resistive heaters 1022, 1024 located proximate to the first and second pluralities of microfluidic channels 1015, 1025. In this example, the resistive heaters can be formed on the substrate or primer layer beneath the microfluidic channels. In other examples, the resistive heaters can also be formed above the microfluidic channels, integrated into sidewalls of the microfluidic channels, or located in another location proximate to the microfluidic channels sufficient to heat fluid in the microfluidic channels. The example shown in FIG. 10 can also include temperature sensors 1032 located proximate to the microfluidic channels. The temperature sensors can measure a temperature of fluid in the microfluidic channels. The location of the temperature sensors can be anywhere sufficient to measure the temperature of the fluid in the microfluidic channels. In this example, the temperature sensors can be formed inside the microfluidic channels to be in direct contact with the fluid.

The resistive heaters and temperature sensors can be used in nucleic acid tests that involve elevated temperatures. In some examples, the resistive heaters and temperature sensors can be electronically connected to a processor to control the temperature of the fluid in the microfluidic channels. In one example, the microfluidic nucleic acid testing device can include electrical contacts connected to the resistive heaters and temperature sensors so that a computer can power and control the resistive heaters and temperature sensors through an interface. The computer can also control the inertial pump resistors to circulate fluid through the microfluidic channels.

When performing a nucleic acid test, in some examples a test fluid can be filled into the first covered fluid feed slot and a control fluid can be filled into the second covered fluid feed slot. The test fluid can be a fluid that may contain a specific target DNA sequence, and the control fluid can be a fluid that is not expected to contain the target sequence. The test fluid can be, for example, an aqueous solution of DNA obtained through any suitable DNA extraction method such as lysis of cells or grinding of a sample of a biological organism. The test fluid and control fluid can be subjected to identical conditions in the first and second microfluidic channels. Because the first and second microfluidic channels can be adjacent one to another, it can be easy to compare the test results of the control fluid and the test fluid. For example, in some tests an optical sensor can be used to detect changes in the fluids being tested. A single optical sensor can capture a view of both the test fluid and the control fluid together, so that a direct comparison can be made.

In further examples, the microfluidic device can also be used for multiplexing tests in which a single sample fluid is tested for multiple different targets. In examples involving nucleic acid testing, a first microfluidic channel can be loaded with the sample fluid mixed with a first set of DNA primers and an adjacent channel can be loaded with the sample fluid mixed with a second set of DNA primers. This can be repeated with any number of additional sets of DNA primers in additional channels to simultaneously test the sample fluid for many different target sequences.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, the term "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context.

As used herein, the term "about" is used to provide flexibility to a numerical range endpoint by providing that a given value may be "a little above" or "a little below" the endpoint. The degree of flexibility of this term can be dictated by the particular variable and determined based on the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

EXAMPLE

Microfluidic Nucleic Acid Testing Device

A microfluidic nucleic acid testing device is constructed according to the design shown in FIG. 10. Inertial pump resistors and resistive heaters are formed on a silicon substrate. A primer layer of SU-8 photoresist is then spin coated onto the substrate, with a thickness of about 4 µm. A microfluidic layer is formed on the primer layer in two steps. In the first step, a 17 µm thick layer of SU-8 is spin coated onto the primer layer. In the second step, a 14 µm thick dry photoresist layer is laminated onto the previous layer. The dry layer is exposed to a UV pattern of the microfluidic features shown in FIG. 10 and developed by dissolving unexposed portions. Temperature sensors are formed inside the microfluidic channels. A top layer is then formed by laminating a 14 µm thick dry photoresist layer over the microfluidic layer. The top layer is exposed to a UV-light pattern defining the fluid feed holes and vent ports. The top layer is then developed by dissolving the unexposed portions.

The size and shape of the microfluidic features in the example device are as follows. The microfluidic channels have a width of 30 µm. The microfluidic channels are spaced so that a minimum wall thickness between the channels is 12 µm. The covered fluid feed slots are formed with a width of 110 µm and a length of 1000 µm. The fluid feed holes are 110 µm×110 µm. Support pillars are formed in the covered fluid feed slots with dimensions of 30 µm×30 µm. The capillary breaks have a narrow opening width of 10 µm. The exterior tapering angle of the capillary breaks is 30° and the interior tapering angle is 15°. The vent ports have a diameter of 10 µm.

In an additional example, a microfluidic nucleic acid testing device is constructed by the same process described above but with covered fluid feed slots having a length of 22,200 µm and fluid feed holes with dimensions of 900 µm×110 µm. The pattern of microfluidic channels shown in FIG. 10 is repeated along the length of the covered fluid feed slots.

While the present technology has been described with reference to certain examples, those skilled in the art will appreciate that various modifications, changes, omissions, and substitutions can be made without departing from the spirit of the disclosure. It is intended, therefore, that the disclosure be limited only by the scope of the following claims.

What is claimed is:
1. A microfluidic device, comprising:
a first covered fluid feed slot in fluid communication with a first microfluidic channel;
a second covered fluid feed slot in fluid communication with a second microfluidic channel;

first and second vent chambers in fluid communication with the first and second microfluidic channels through first and second capillary breaks, wherein the first and second capillary breaks comprise tapered portions and narrowed openings with a smaller width than a width of the first and second microfluidic channels; and first and second vent ports to vent gas from the first and second vent chambers, wherein the first and second vent ports are located a distance away from the first and second capillary breaks such that fluid in the capillary breaks does not escape through the first and second vent ports, wherein the first microfluidic channel is formed adjacent to the second microfluidic channel but not in fluid communication with the second microfluidic channel, wherein the first covered fluid feed slot includes a first fluid feed hole for filling a fluid into the first covered fluid feed slot, and wherein the second covered fluid feed slot includes a second fluid feed hole for filling a fluid into the second covered fluid feed slot.

2. The device of claim 1, wherein the first fluid feed hole has a smaller area than the first covered fluid feed slot and the second fluid feed hole has a smaller area than the second covered fluid feed slot.

3. The device of claim 1, wherein the first microfluidic channel is one of a first plurality of parallel microfluidic channels in fluid communication with the first covered fluid feed slot, and the second microfluidic channel is one of a second plurality of parallel microfluidic channels in fluid communication with the second covered fluid feed slot.

4. The device of claim 1, wherein the first microfluidic channel and second microfluidic channel have a serpentine shape with a plurality of turns.

5. The device of claim 1, wherein the first microfluidic channel is formed as a loop connecting to the first covered fluid feed slot at both ends, and wherein the second microfluidic channel is formed as a loop connecting to the second covered fluid feed slot at both ends.

6. The device of claim 1, further comprising inertial pumps in the first and second microfluidic channels to pump fluid from the first and second covered fluid feed slots into the first and second microfluidic channels.

7. The device of claim 1, further comprising a first plurality of microfluidic channels connecting the first covered fluid feed slot to the first vent chamber through capillary breaks, and a second plurality of microfluidic channels connecting the second covered fluid feed slot to the second vent chamber through capillary breaks.

8. The device of claim 7, wherein the first plurality of microfluidic channels and the second plurality of microfluidic channels are interdigitated in an area between the first covered fluid feed slot and the second covered fluid feed slot.

9. A microfluidic nucleic acid testing device, comprising:
a first covered fluid feed slot in fluid communication with a first microfluidic channel;
a second covered fluid feed slot in fluid communication with a second microfluidic channel;
first and second vent chambers in fluid communication with the first and second microfluidic channels through first and second capillary breaks wherein the first and second capillary breaks comprise tapered portions and narrowed openings with a smaller width than a width of the first and second microfluidic channels;
first and second vent ports to vent gas from the first and second vent chambers, wherein the first and second vent ports are located a distance away from the first and second capillary breaks such that fluid in the capillary breaks does not escape through the first and second vent ports; and one or more heating resistors located proximate to the first and second microfluidic channels capable of heating a fluid in the microfluidic channels;

wherein the first microfluidic channel is formed adjacent to the second microfluidic channel but not in fluid communication with the second microfluidic channel, wherein the first covered fluid feed slot includes a first fluid feed hole for filling a fluid into the first covered fluid feed slot, the first fluid feed hole having a smaller area than the first covered fluid feed slot, and wherein the second covered fluid feed slot includes a second fluid feed hole for filling a fluid into the second covered fluid feed slot, the second fluid feed hole having a smaller area than the second covered fluid feed slot.

10. The microfluidic nucleic acid testing device of claim 9, further comprising one or more temperature sensors located proximate to the first and second microfluidic channels capable of measuring a temperature of a fluid in the microfluidic channels.

11. The microfluidic nucleic acid testing device of claim 9, wherein the first microfluidic channel is formed as a loop connecting to the first covered fluid feed slot at both ends, and wherein the second microfluidic channel is formed as a loop connecting to the second covered fluid feed slot at both ends.

12. The microfluidic nucleic acid testing device of claim 9, wherein the device further comprises inertial pumps in the first and second microfluidic channels to circulate fluid through the first and second microfluidic channels.

13. The microfluidic nucleic acid testing device of claim 9, wherein the first fluid feed hole has a smaller area than the first covered fluid feed slot and the second fluid feed hole has a smaller area than the second covered fluid feed slot.

14. The microfluidic nucleic acid testing device of claim 9, wherein the first microfluidic channel is one of a first plurality of parallel microfluidic channels in fluid communication with the first covered fluid feed slot, and the second microfluidic channel is one of a second plurality of parallel microfluidic channels in fluid communication with the second covered fluid feed slot.

15. The microfluidic nucleic acid testing device of claim 9, wherein the first microfluidic channel and second microfluidic channel have a serpentine shape with a plurality of turns.

16. The microfluidic nucleic acid testing device of claim 9, further comprising a first plurality of microfluidic channels connecting the first covered fluid feed slot to the first vent chamber through capillary breaks, and a second plurality of microfluidic channels connecting the second covered fluid feed slot to the second vent chamber through capillary breaks.

17. The microfluidic nucleic acid testing device of claim 16, wherein the first plurality of microfluidic channels and the second plurality of microfluidic channels are interdigitated in an area between the first covered fluid feed slot and the second covered fluid feed slot.

18. A microfluidic device, comprising:
a first covered fluid feed slot including a first fluid feed hole for filling a fluid into the first covered fluid feed slot, the first fluid feed hole having a smaller area than the first covered fluid feed slot;

a second covered fluid feed slot oriented parallel to the first covered fluid feed slot, the second covered fluid feed slot including a second fluid feed hole for filling a fluid into the second covered fluid feed slot, the second fluid feed hole having a smaller area than the second covered fluid feed slot;

a first series of microfluidic channel bundles connecting to the first covered fluid feed slot; and a second series of microfluidic channel bundles connecting to the second covered fluid feed slot, wherein the first and second series of microfluidic channel bundles are interdigitated in an area between the first and second covered fluid feed slots, wherein the first series of microfluidic channel bundles are formed adjacent to the second series of microfluidic channel bundles but not in fluid communication with the second series of microfluidic channel bundles, wherein the first series of microfluidic channel bundles and the second series of microfluidic channel bundles each comprise a plurality of microfluidic channels connected to a vent chamber through capillary breaks, wherein the capillary breaks comprise tapered portions and narrowed openings with a smaller width than a width of the microfluidic channels, and wherein the vent chamber is in fluid communication with a vent port to vent gas from the vent chamber, wherein the vent port is located a distance away from the capillary breaks such that fluid in the capillary breaks does not escape through the vent port.

* * * * *